United States Patent
Almond et al.

(10) Patent No.: US 7,722,570 B2
(45) Date of Patent: May 25, 2010

(54) SURGICAL SEAL

(75) Inventors: Edward Almond, Leeds (GB); Peter Moran, Leeds (GB)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 1549 days.

(21) Appl. No.: 10/849,574

(22) Filed: May 18, 2004

(65) Prior Publication Data

US 2004/0215209 A1    Oct. 28, 2004

Related U.S. Application Data

(63) Continuation of application No. 09/866,461, filed on May 24, 2001, now abandoned.

(30) Foreign Application Priority Data

May 24, 2000  (GB)  .................................. 0012461.0

(51) Int. Cl.
*A61M 5/178*    (2006.01)
(52) U.S. Cl. ............................. 604/167.06; 604/167.01; 604/256
(58) Field of Classification Search ............. 604/23–26, 604/108, 164.01, 167.01–167.06, 256; 277/605, 277/607, 609, 616; 251/1.1, 1.2, 212; 606/167
See application file for complete search history.

(56) References Cited

U.S. PATENT DOCUMENTS

| 3,920,215 | A |   | 11/1975 | Knauf |
|---|---|---|---|---|
| 4,513,948 | A | * | 4/1985 | Konig ......................... 251/212 |
| 5,209,737 | A | * | 5/1993 | Ritchart et al. .......... 604/167.03 |
| 5,603,702 | A |   | 2/1997 | Smith et al. |
| 5,820,600 | A | * | 10/1998 | Carlson et al. .......... 604/167.03 |
| 7,025,747 | B2 | * | 4/2006 | Smith .................... 604/167.06 |

FOREIGN PATENT DOCUMENTS

| DE | 3915597 C1 |   | 5/1990 |
|---|---|---|---|
| EP | 0426407 A2 |   | 5/1991 |
| EP | 0630660 A1 | * | 12/1994 |

* cited by examiner

*Primary Examiner*—Kevin C Sirmons
*Assistant Examiner*—Laura C Schell
(74) *Attorney, Agent, or Firm*—John F. Heal; David G. Majdali; James E. Austin (57) ABSTRACT

A seal for laparoscopic port comprising:
  a base adapted to engage a cannula, the base including an axial aperture for a surgical instrument;
  a multiplicity of jaws mounted on the base, the jaws being moveable radially with respect to the aperture between an open position wherein the shaft of the surgical instrument may pass freely and the closed position wherein the jaws engage said shaft and provide a restraining force restraining radial movement of the shaft; and
  an actuator rotatable to urge the jaws to move between said open position and said closed position.

14 Claims, 9 Drawing Sheets

SURGICAL SEAL

CROSS REFERENCE TO RELATED APPLICATIONS

This application is a continuation of prior application Ser. No.: 09/866,461, filed on May 24, 2001 now abandoned, entitled, "SURGICAL SEAL" by Edward Almond and Peter Moran, which further claims priority to Great Britain Application No.: 0012461.0, filed May 24, 2000, entitled, "SURGICAL SEAL" by Edward Almond and Peter Moran.

This invention relates to a seal for use with a surgical instrument to provide a gas tight seal through which the instrument may pass. The invention relates particularly but not exclusively to a seal for a laparoscopic port.

Laparoscopic procedures are performed through a small incision, usually through narrow endoscopic tubes or cannulae inserted through a small entrance incision in the skin. An instrument inserted into the body must be sealed to ensure that gases do not enter or exit through the incision, for example in procedures in which the surgical region is insufflated. The introduction of a tube into an anatomical cavity such as the abdominal cavity is usually achieved using a trocar and cannula assembly. The cannula assembly may comprise a cannula attached to a cannula housing which generally includes a valve assembly adapted to maintain a seal across the opening of the valve assembly both with and without an instrument inserted through it. Various valve systems for cannula assemblies have been proposed, for example in U.S. Pat. Nos. 5,209,737, 5,308,336, 5,385,553 and 5,545,142. 5,603,702 discloses a complex structure with several hinged guard members disposed in an overlapping petal-like arrangement. U.S. Pat. Nos. 5,407,433 and 5,411,483 disclose universal seals for laparoscopic ports. However these suffer from the disadvantage that the entire seal can move in an orbital manner. This can cause failure of the seal between the gasket and instrument during surgery.

Furthermore the friction between thee annular gasket of U.S. Pat. No. 5,411,483 and the shaft of the instrument depends on the diameter of the shaft. High frictional forces are undesirable because they impede free movement of the instrument during surgery.

According to the present invention a seal for a laparoscopic port comprises:

a base adapted to engage a cannula, the base including an axial aperture for a surgical insturment;

a multiplicity of jaws mounted on the base, the jaws being moveable radially with respect to the aperture between an open position wherein a shaft of the surgical instrument may pass freely and a closed position wherein the jaws engage said shaft and provide a restraining force restraining radial movement of the shaft; and actuator rotatable to urge the jaws to move between said open position and said closed position.

In preferred embodiments the jaws may engage or restrain shafts having different diameters. In this way a single seal may be used with several instruments. In particularly preferred embodiments the jaws may be adjusted to engage a shaft having any diameter between preselected upper and lower limits.

The jaws are preferably moveable along guides provided on the carrier plate. The guides may constitute channels between raised formations, tracks or runners. Each jaw preferably comprises a follower member adapted to be received in a respective guideway in the actuator arranged so that rotation of the actuator causes radial movement of the jaw.

In a particularly preferred embodiment of the invention each guideway comprises an arcuate channel formed in the actuator, a projection or other follower being received in the channel.

The channels may have the configuration of parabolic curves.

The seal of this invention may include a diaphragm adapted to contact the shaft of a surgical instrument extending through the aperture. The diaphragm preferably includes a lip, each jaw including a radially outwardly facing portion adapted to engage the lip so that the aperture of the diaphragm is forced to open as the jaws move to the open position.

The aperture of the jaws is preferably continuously adjustable between maximum and minimum positions. This allows the seal to accommodate various sizes of instrument shafts. A further advantage is that the jaws may be opened to facilitate removal of tissue samples during a surgical procedure.

Seals in accordance with this invention may be used with a variety of laparoscopic instruments. Most instruments have a smooth coaxial point at the distal end to facilitate insertion through the cannula and seal. However spiked instruments, for example clip applicators or pyramidal trocars may damage the diaphragm as the instrument is inserted through the seal.

In preferred embodiments of this invention a multiplicity of shield members are disposed on the proximal side of the diaphragm to prevent accidental damage to the diaphragm. The shield members are preferably moveable radially between open and closed positions in the same direction and at the same time, that is synchronously with the jaws. Preferably each shield member is attached to a respective jaw.

The shield members may be interleaved to form a continuous barrier covering the diaphragm, for example arranged like the petals of an iris shaped configuration. Alternatively the shield members may be in alternating forward and backward axial disposition to form a continuous interleaved barrier.

In a particularly preferred embodiment each jaw member has two laterally extending wing-like shield flanges arranged to extend generally circumferentially of the surgical instrument receiving aperture, one or more shield members being axially forward of the other to engage a complimentary shield member on an adjacent jaw.

The actuator may be arranged so that the jaws may be fully opened or closed by a rotation through an angle of 30 to 180°. This makes it easy for a surgeon to open or close the jaw using his fingers but without rotation of the wrist.

A top cover may be placed over the actuator to prevent occlusion of the moving parts and ingress of dirt during use.

Any convenient number of jaws may be provided, preferably at least 5 or more, more preferably 6 to 8, most preferably 7.

The invention is further described by means of example but not in any limitative sense with reference to the accompanying drawings of which.

The seal illustrated in the Figures comprises a base 1 having a locking device 2 adapted to facilitate attachment to a cannula. In an alternative embodiment of the invention on the base 1 may be integral with a cannula.

Figure 1:
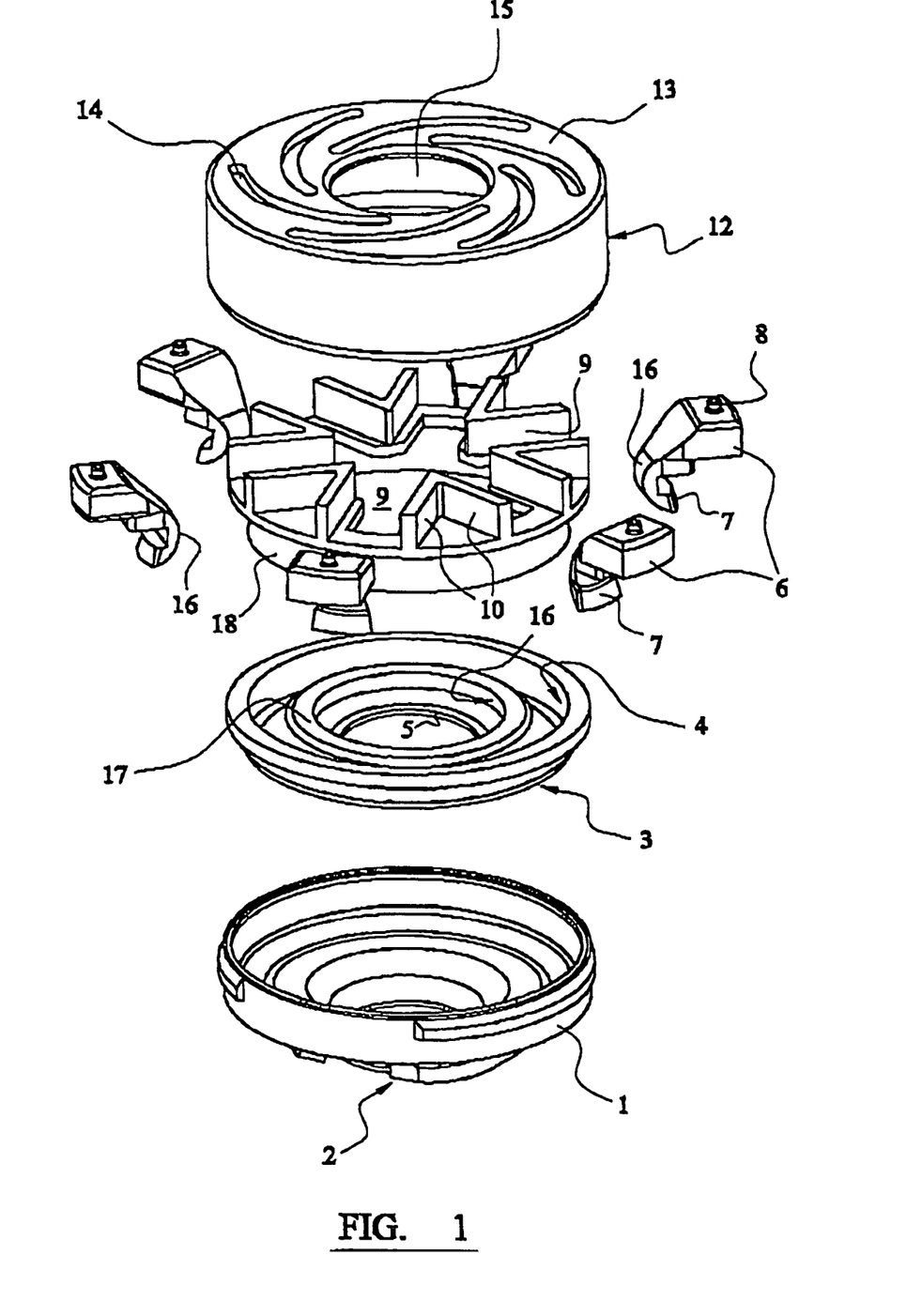
FIG. 1 is an exploded view of a seal in accordance with the invention.

A diaphragm or gasket 3 composed of elastomeric material lies within the base 1. The diaphragm includes an inner surface 4 adapted to receive the base of a carrier plate 18. An annular lip 5 is adapted to receive and form a gas tight seal with the shaft of an instrument (not shown). The inwardly facing surface 16 of a flange 17 extends axially from the diaphragm adjacent the rim 5. Outward movement of the flange 17 opens the aperture defined by the rim 5.

The carrier plate 18 includes a multiplicity of guideways 9 formed by axially extending runners 9. A moveable jaw member 6 can move radially within each guide way 9 in use. In the illustrated embodiment there are six jaws. Each jaw contains a radially inwardly facing tooth 16 and radially outwardly facing hook portion 7. The hook portion 7 engages the surface 16 of the diaphragm flange 17. The tooth portion 16 of each jaw serves to engage the shaft of a surgical instrument passing through the seal. A lug 8 extending axially from the upper surface of the jaw as shown is received in a channel 14 of the upper surface 13 of the actuator 12. The actuator has a generally cylindrical outer surface which may be rotated manually by a surgeon in use. The channels 14 each have a parabolic curved configuration and are spaced equidistantly around the upper surface 13 of the actuator. The configuration of the channels 14 may have the general form of a iris. Rotation of the actuator 12 causes the lugs and consequently the jaws to move radially inwardly or outwardly relative to the carrier 18. Accordingly the teeth 16 of the jaws 6 may move into and out of engagement with a shaft (not shown) extending through the aperture 15 of the seal. During opening of the jaws, the hooked portion 7 dilate the lip 5 of the gasket so that a generally even frictional force is encountered irrespective of the diameter of the shaft.

Figure 2:
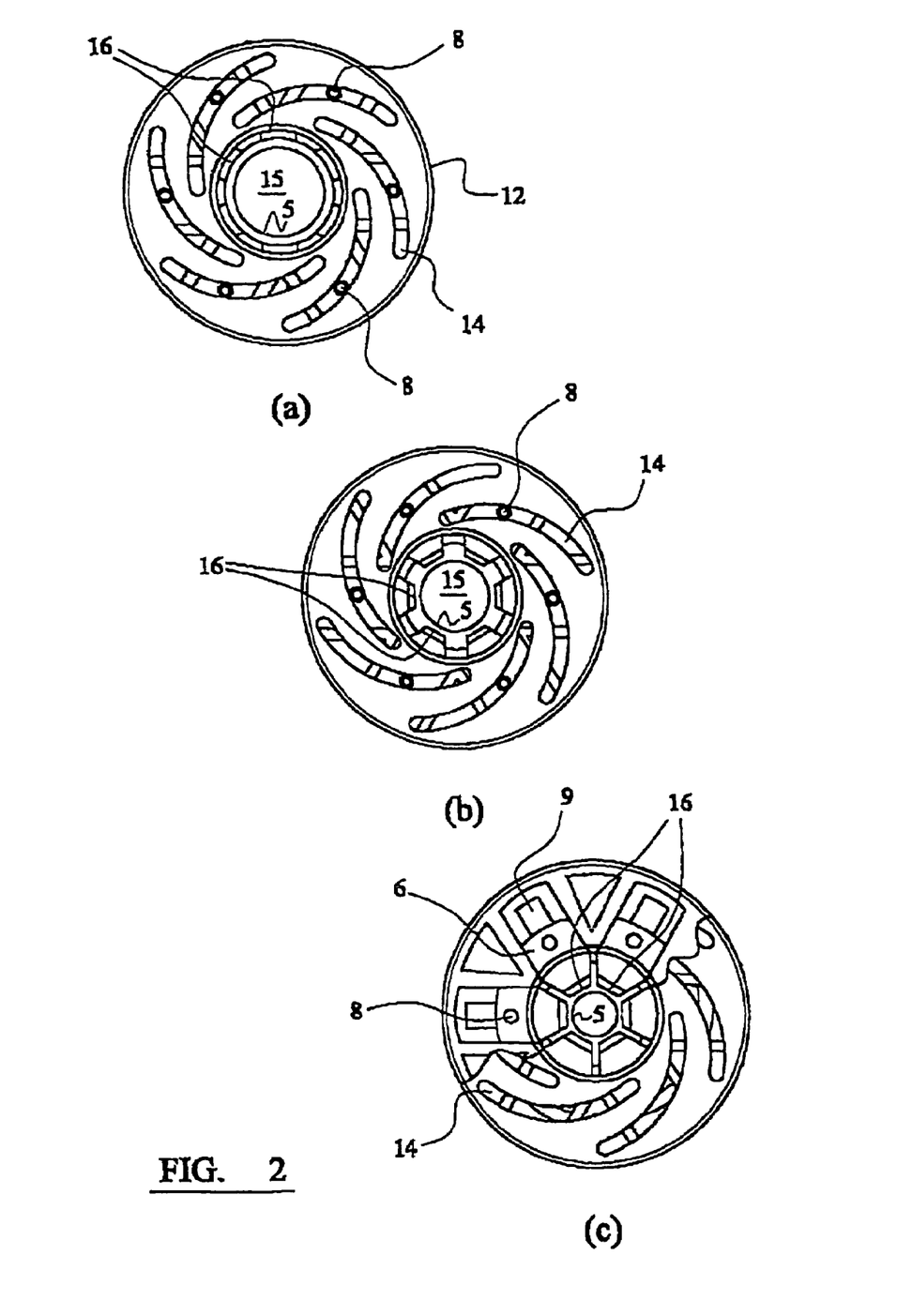
FIG. 2 represents three plan views of the seal.

FIGS. 2*a*, *b* and *c* show the seal with the jaws in different positions. The same reference numerals are used to denote like components in FIGS. 1, 2 and 3.

In FIG. 2*a* the jaws are open with the teeth 16 retracted. When the seal is engaged to a cannula, rotation of the actuator 12 in a clockwise direction causes the lugs 8 and consequently the jaws to move radially inwardly as shown in FIG. 2*b*.

FIG. 2*c* is a partially cut away view illustrating the jaws in the closed position.

Figure 3:
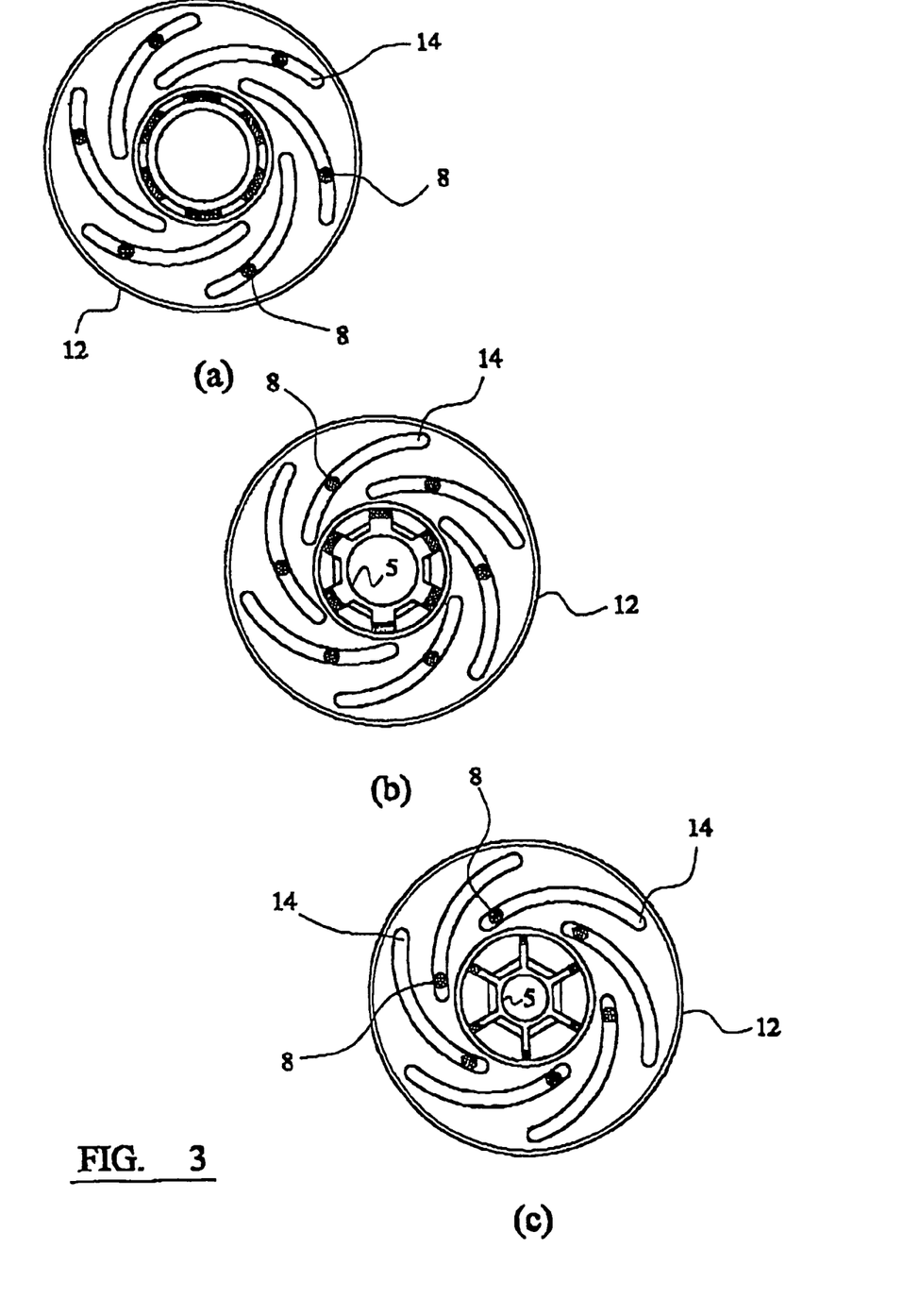
FIG. 3 represents three plan views of the seal illustrating closing of the jaws.

The relative positions of the lugs 8 in the channels 14 are shown in FIGS. 3*a*, *b* and *c*. In FIG. 3*c* the lugs are at the inner-most ends of the channels 14 so that the jaws are closed to the maximum extent. Rotation of the actuator 12 shown in FIG. 3*c* in an anti-clockwise direction causes the jaws to move radially outwardly. Full opening of the jaws is achieved by rotation of the actuator through about 60°.

The curvature of the channels 14 is selected so that outward pressure on a jaw by lateral movement of the shaft of the surgical instrument is sufficient to overcome frictional forces within the seal. Accordingly lateral movement of the shaft cannot open the jaws. The shaft is securely held and cannot move in an orbital motion to break the seal with the gasket lip 5. Similarly a larger diameter shaft which engages the jaws in FIG. 3*b* is also securely held. However the jaws may be easily opened by a surgeon to facilitate removal of the instrument, for example with a tissue sample of a larger diameter than the shaft.

The seal of this invention may incorporate a top cover, for example formed from transparent waterproof material to prevent ingress of dirt or physiological material between the moving surfaces of the seal.

FIGS. 4 to 8 illustrate a preferred seal for a laparoscopic port in accordance with this invention. The arrangement is generally similar to that shown in FIGS. 1 to 3.

Figure 4:
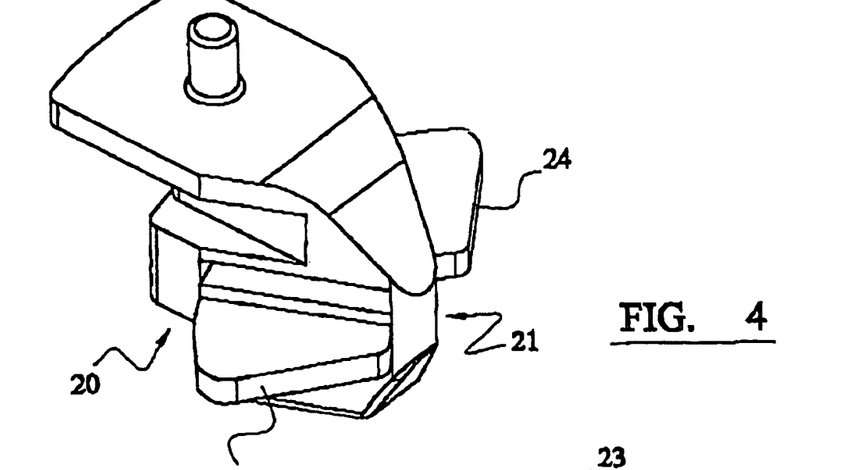
FIG. 4 is a perspective view of a jaw of a seal in accordance with a preferred embodiment of the invention.
Figure 5:
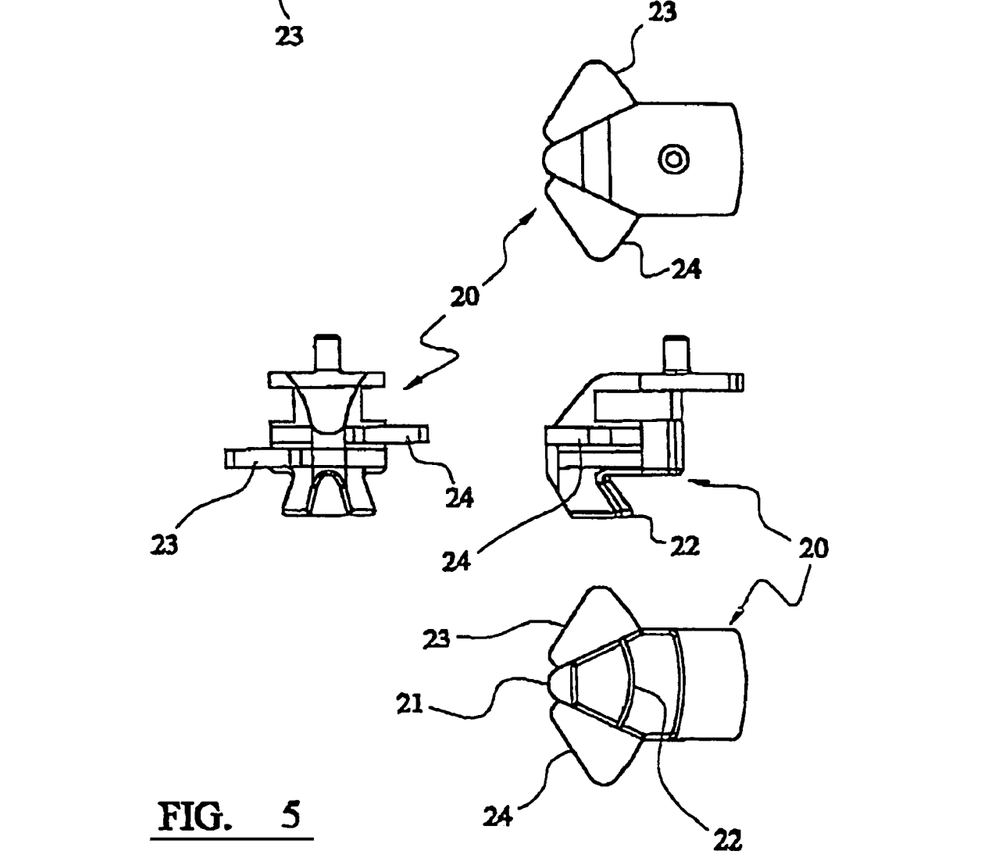
FIG. 5 shows plan and elevational views on reduced scale of the jaw shown in FIG. 4.

The moveable jaw member 20 shown in FIGS. 4 and 5 include a radially inwardly facing tooth 21 and a radially outwardly facing hook portion 22. The hook portion is arranged to engage the surface of the diaphragm, not shown. The jaw member 20 has flange shaped shield members 23, 24 extending laterally from the jaw member so that the shield members extend generally circumferentially of the axially extending instrument receiving aperture.

Figure 6:
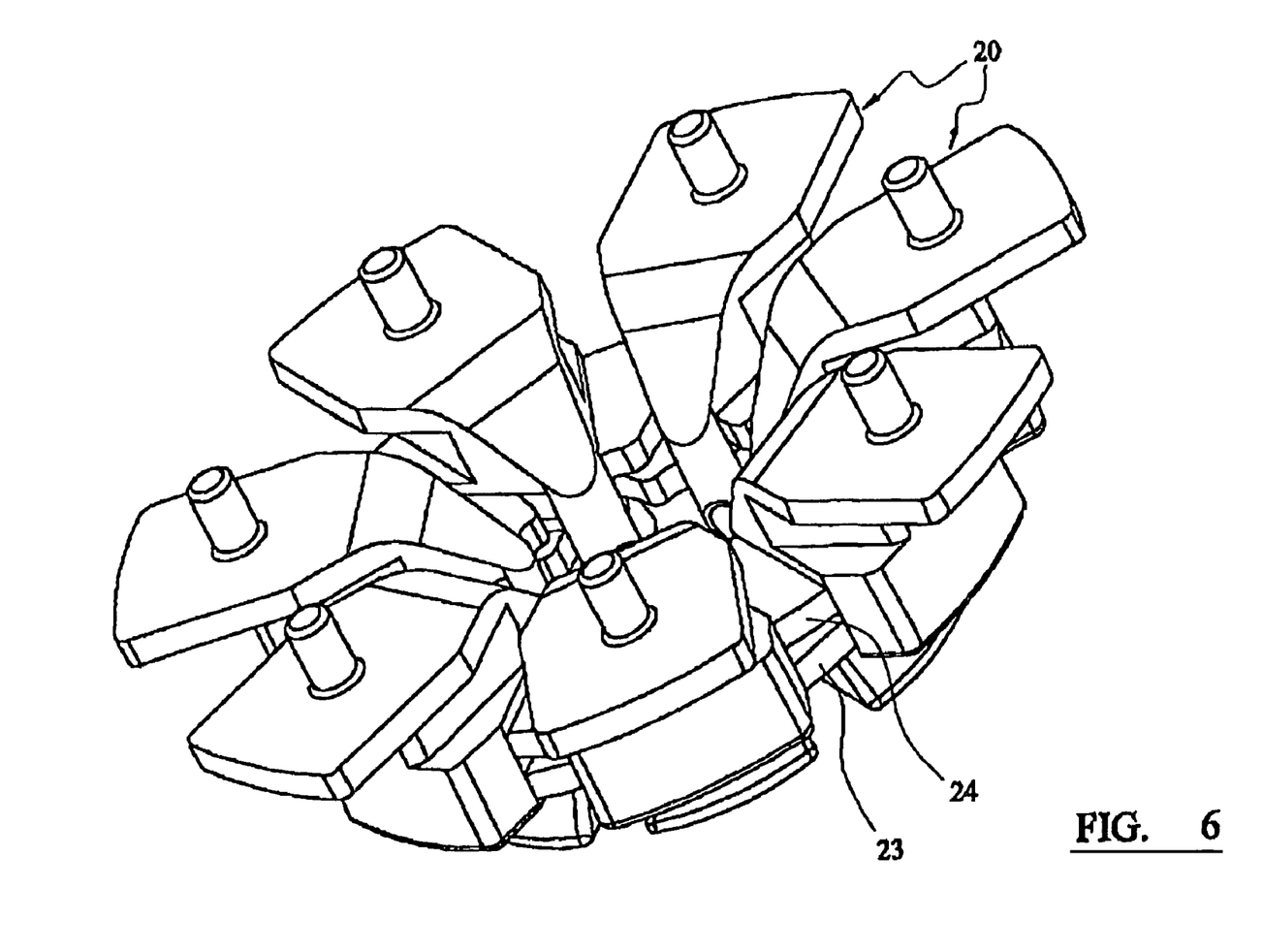
FIG. 6 shows an assembly of seven jaws in a circular array.

The jaws are arranged to form a circular array, for example comprising 7 jaws as shown in FIG. 6. This shield member 23 is disposed axially distally of the shield member 24 so that it underlies a radially inwardly extending ring 24 of an adjacent jaw as shown in FIG. 6. In this way a continuous annular shield is formed protecting the less flexible body of the diaphragm 26 from damage by a trocars or other pointed instrument.

Figure 7:
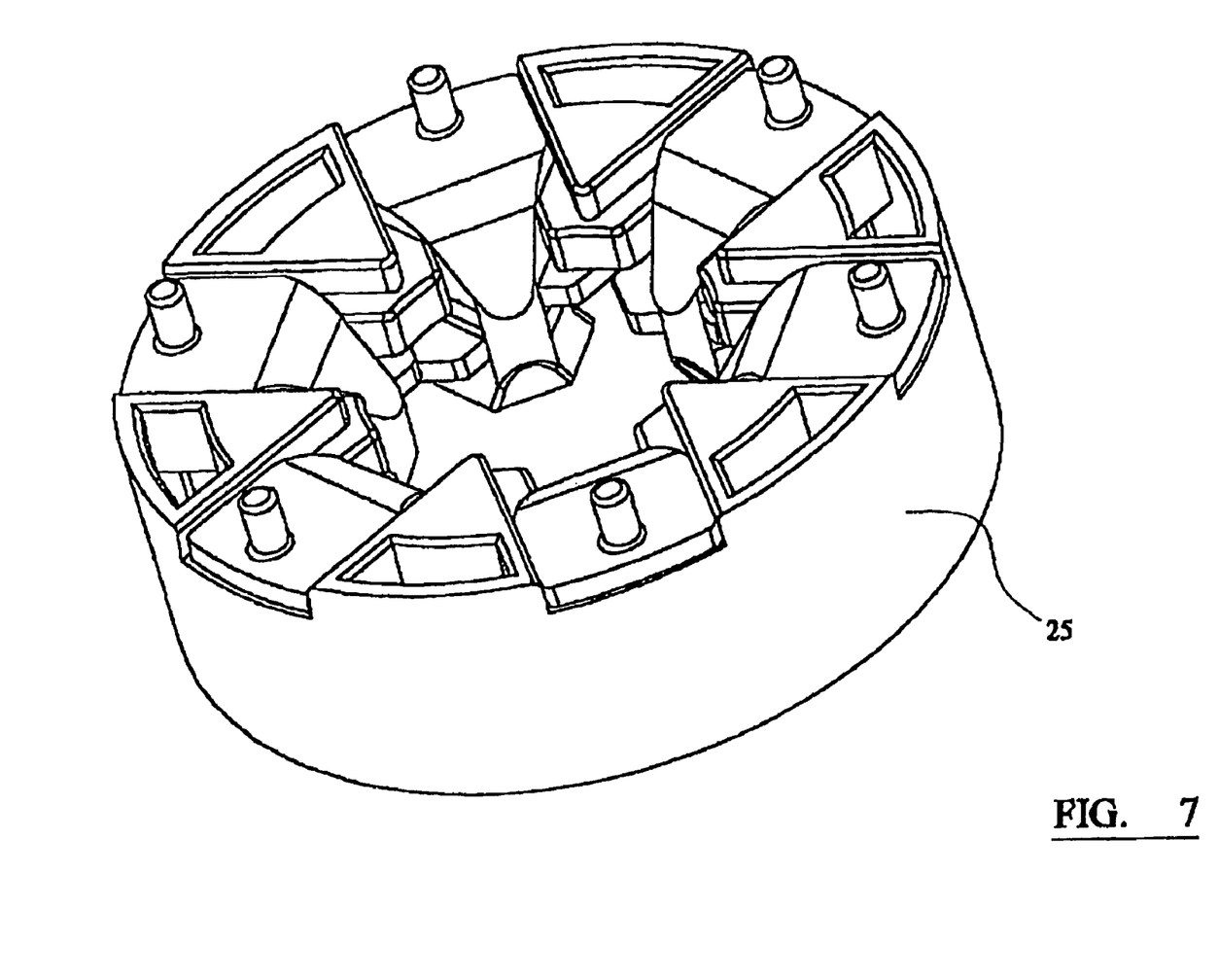
FIG. 7 shows the array of jaws of FIG. 6 contained in the carrier plate.

FIG. 7 shows the jaws located in the carrier plate 25. The jaws are each able to slide radially within guideways in the carrier plate.

Figure 8:
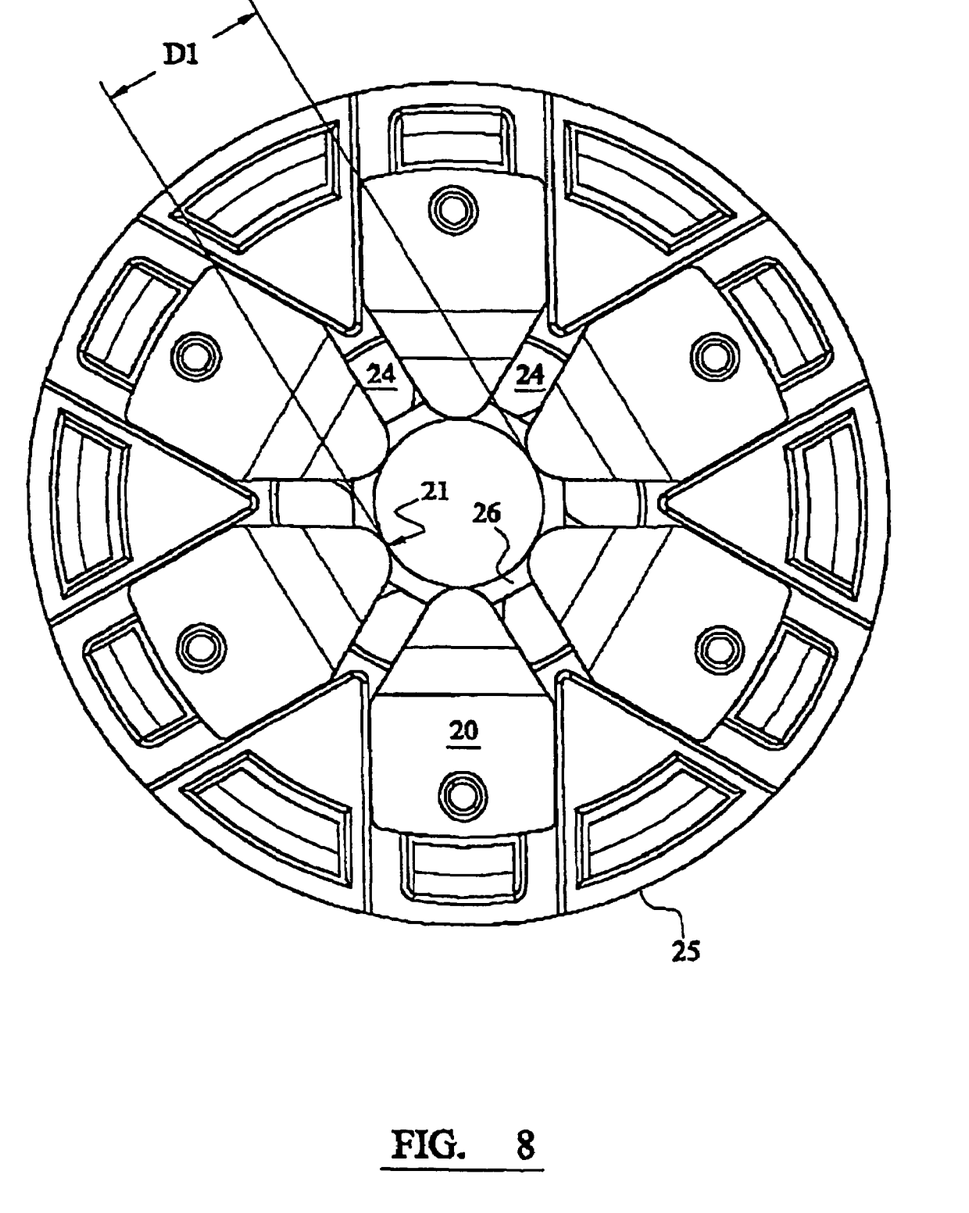
FIGS. 8 to 10 are plan views illustrating the opening of the jaws.
Figure 9:
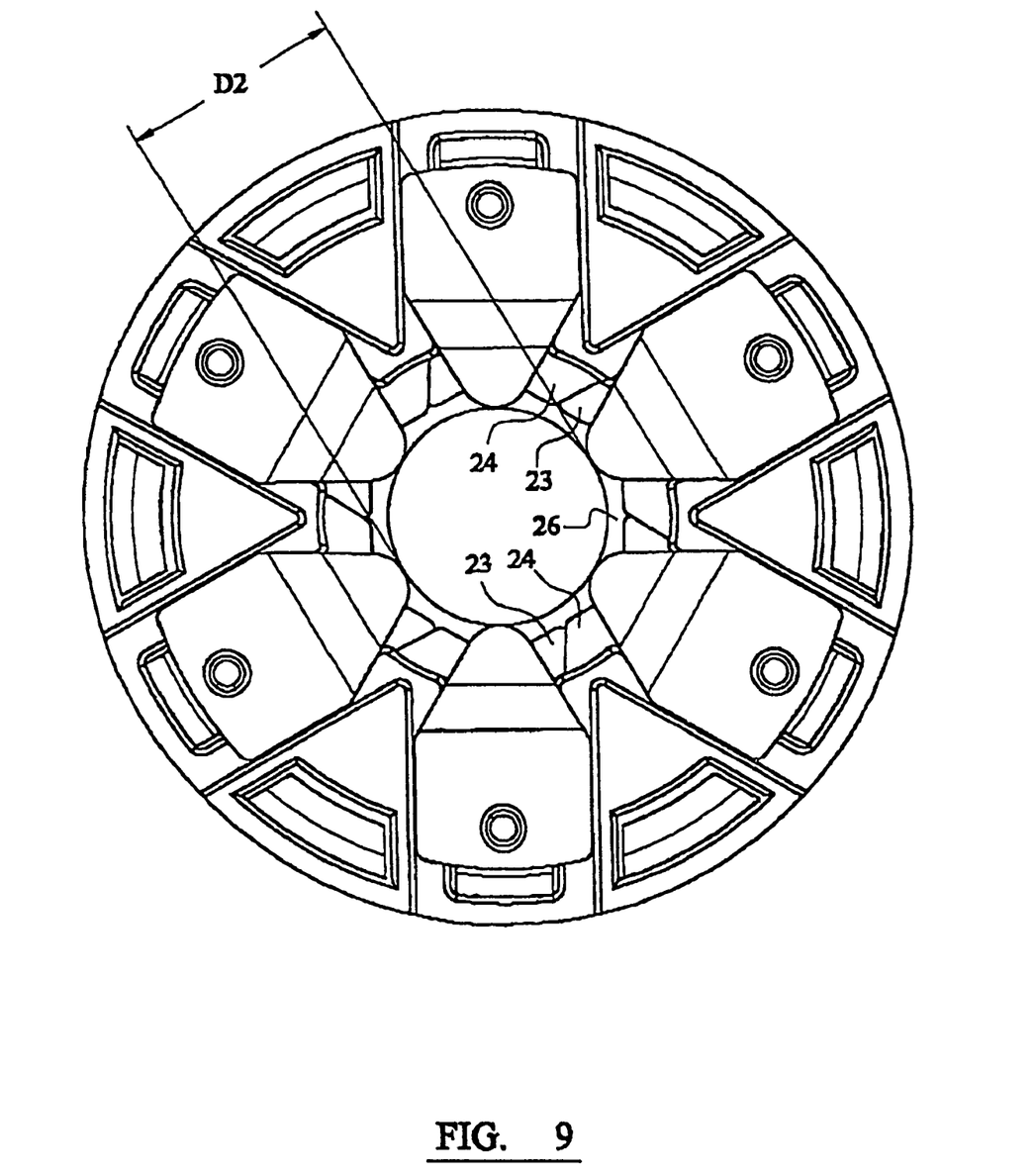
Figure 10:
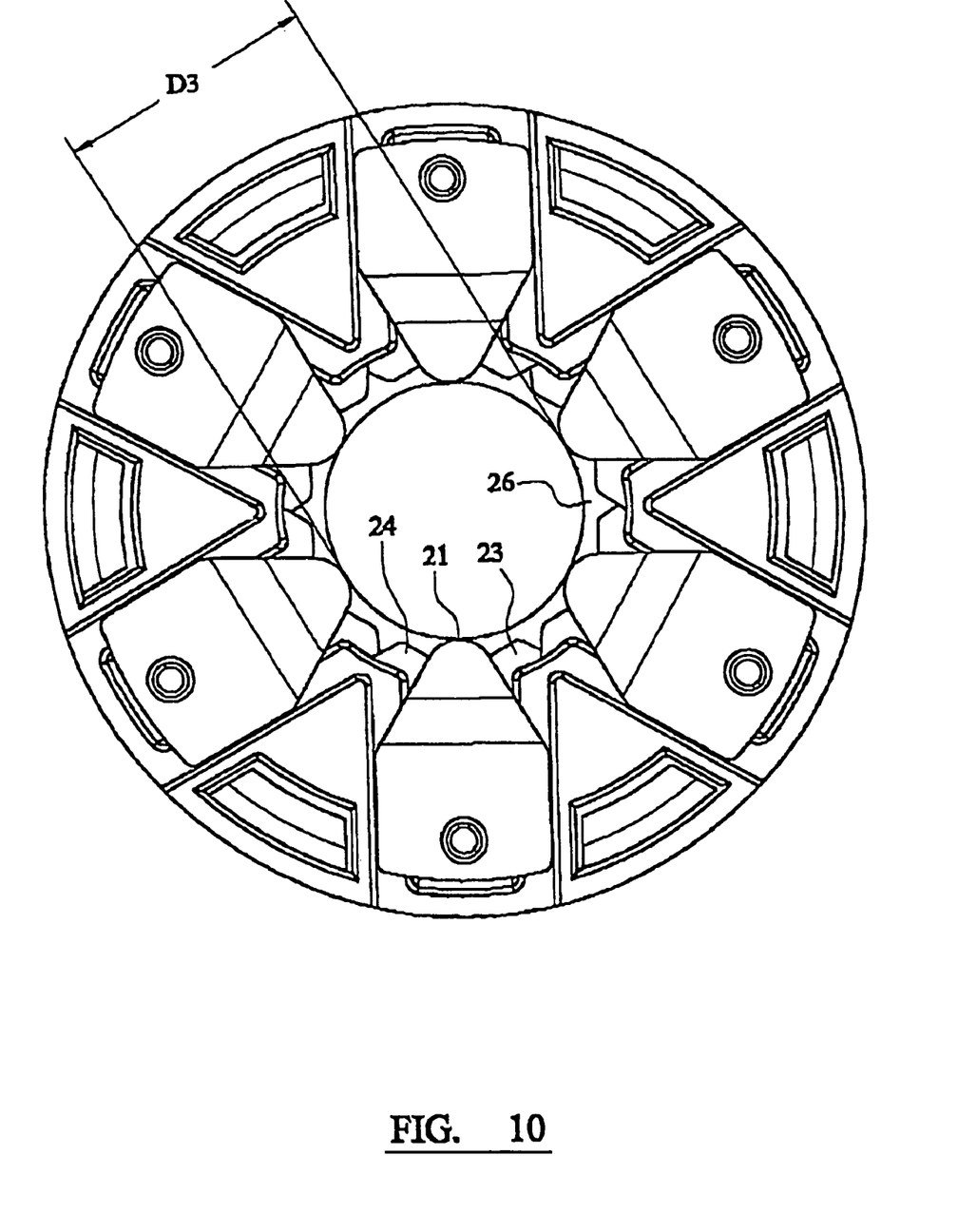

FIGS. 8 to 10 show successive stages in opening of the jaws within the carrier plate 25. The hooked portions 22 (not visible in FIGS. 8 to 10) engage a complementary ring in the diaphragm 26 (opening the central aperture as the jaws are withdrawn). In FIG. 8 the central aperture has a small diameter D1 and the shield members 24 almost completely cover the underlying diaphragm. In FIG. 9 a larger diameter aperture D2 results from opening of the jaws exposing the underlying, radially outward shield members 23. The shield members 23, 24 define a seven sided polygonal configuration.

In FIG. 10 a maximum diameter aperture D3 results from full opening of the jaws exposing the shield members 23, 24 to a maximum extent.

The invention claimed is:

1. A seal for laparoscopic port comprising:
   a base adapted to engage a cannula, the base including an axial aperture for a surgical instrument and a plurality of guides;
   a multiplicity of jaws mounted on the base, the jaws being moveable radially along the plurality of guides with respect to the aperture between an open position wherein the shaft of the surgical instrument may pass freely and the closed position wherein the jaws engage said shaft and provide a restraining force restraining radial movement of the shaft, and the multiplicity of jaws each comprising a follower member extending therefrom;
   an actuator, the actuator having a plurality of guideways formed therein, the follower member of each of the multiplicity of jaws being received in a corresponding one of the plurality of guideways, the actuator rotatable to urge the jaws to move between said open position and said closed position; and
   a diaphragm adapted to contact the shaft of a surgical instrument extending through the aperture;
   wherein the diaphragm includes a lip, each jaw including a radially outwardly facing portion adapted to engage the lip so that the aperture of the diaphragm is forced to open as the jaws move to an open position.

2. A seal as claimed in claim 1, wherein the jaws may be adjusted to engage a shaft having any diameter between preselected upper and lower limits.

3. A seal as claimed in claim 1 wherein the guides on the base comprise channels between raised formations, tracks or runners.

4. A seal as claimed in claim 1, wherein the follower member of each jaw comprises a lug adapted to be received in the corresponding guideway in the actuator arranged so that rotation of the actuator causes radial movement of the jaw.

5. A seal as claimed in claim 1, wherein each guideway in the actuator comprises an arcuate channel formed in the actuator.

6. A seal as claimed in claim 5, wherein the channels have the configuration of parabolic curves.

7. A seal as claimed in claim 1, wherein the radially outwardly facing portion of each jaw comprises a hook.

8. A seal as claimed in claim 1, wherein the aperture of the jaws is continuously adjustable between maximum and minimum positions.

9. An actuator as claimed in claim 1, wherein the jaws may be fully opened or closed by a rotation through an angle of 30 to 180°.

10. A seal as claimed in claim 1, including a multiplicity of shield members disposed on the proximal side of the diaphragm to prevent accidental damage to the diaphragm in use.

11. A seal as claimed in claim 10, wherein the shield members are moveable radially between open and closed positions synchronously with the jaws.

12. A seal as claimed in claim 11, wherein each shield member is attached to a respective jaw.

13. A seal as claimed in claim 12, wherein the shield members are interleaved to form a continuous barrier covering the diaphragm.

14. A seal as claimed in claim 1, wherein each jaw member has two laterally extending shield members.

\* \* \* \* \*